(12) United States Patent
Lee et al.

(10) Patent No.: US 9,868,874 B2
(45) Date of Patent: Jan. 16, 2018

(54) SYMPATHETIC PRINTED-MATTER AND METHOD OF PRODUCING THE SAME

(71) Applicants: KANGWON NATIONAL UNIVERSITY University-Industry Cooperation Foundation, Gangwon-do (KR); Daehan Paper Co.,Ltd., Chungcheongbuk-do (KR); Taekyung Polymer Co., Ltd., Gyeonggi-do (KR); CENTRE TECHNIQUE DE L' INDUSTRIE DES PAPIERS, CARTONS ET CELLULOSES, Grenoble (FR)

(72) Inventors: Myoung Ku Lee, Gangwon-do (KR); Jeong Yong Ryu, Gangwon-do (KR); Chang Geun Kim, Gangwon-do (KR); Kwang Seob Lee, Gangwon-do (KR); Jae Hoon Lee, Gangwon-do (KR); Han Je Cho, Seoul (KR); Hyeok Jun Kwon, Gyeonggi-do (KR); David Guerin, Grenoble (FR); Philippe Martinez, Grenoble (FR)

(73) Assignees: KANGWON NATIONAL UNIVERSITY-INDUSTRY COOPERATION FOUNDATION, Gangwon-Do (KR); DAEHAN PAPER CO., LTD., Chungcheongbuk-Do (KR); TAEKYUNG POLYMER CO., LTD., Gyeonggi-Do (KR); CENTRE TECHNIQUE DE L'INDUSTRIE DES PAPIERS, CARTONS ET CELLULOSES, Grenoble (FR)

( * ) Notice: Subject to any disclaimer, the term of this patent is extended or adjusted under 35 U.S.C. 154(b) by 0 days.

(21) Appl. No.: 15/223,490

(22) Filed: Jul. 29, 2016

(65) Prior Publication Data
US 2017/0137654 A1    May 18, 2017

(30) Foreign Application Priority Data

Nov. 13, 2015 (KR) ........................ 10-2015-0159856

(51) Int. Cl.
*B41M 3/14* (2006.01)
*C09D 11/04* (2006.01)
(Continued)

(52) U.S. Cl.
CPC .............. *C09D 11/50* (2013.01); *B41F 17/00* (2013.01); *B41M 3/14* (2013.01); *C09D 11/04* (2013.01);
(Continued)

(58) Field of Classification Search
CPC ........... B41M 3/14; C09D 11/04; C09D 11/50
(Continued)

(56) References Cited

U.S. PATENT DOCUMENTS 3,926,645 A    12/1975  Strahl ............................. 106/21
6,342,268 B1    1/2002  Samain ...................... 427/248.1
(Continued)

FOREIGN PATENT DOCUMENTS

KR            0173103       12/1999
KR      10-2015-0077379      7/2015
(Continued)

OTHER PUBLICATIONS

European Search Report from corresponding European Application No. EP16185655, Mar. 23, 2017.
(Continued)

*Primary Examiner* — Bruce H Hess
(74) *Attorney, Agent, or Firm* — Harness, Dickey & Pierce, P.L.C.

(57) ABSTRACT

Using the sympathetic printed-matter according to the present invention, a hidden content can be visualized just by
(Continued)

wetting. Therefore, it is possible to remove necessities of the sympathetic ink and a special material such as reagent or equipment for visualizing hidden contents. In addition, since the hidden contents disappear by removing water from the sympathetic printed-matter, the sympathetic printed-matter can be used repeatedly. Using the reading confirmation portion, whether or not the sympathetic printed-matter has been read by any other person can be easily determined. In the sympathetic printing method according to the present invention, a hydrophobic substrate can be formed using an existing gas grafting facility, and an ester hydrolase composition and the reading confirmation portion can be formed using an existing printing method. Therefore, a large amount of sympathetic printed-matters can be produced inexpensively and efficiently.

12 Claims, 1 Drawing Sheet

(51) Int. Cl.
    *C09D 11/50*      (2014.01)
    *C12N 9/16*      (2006.01)
    *C12N 9/18*      (2006.01)
    *B41F 17/00*      (2006.01)

(52) U.S. Cl.
    CPC ................. *C12N 9/16* (2013.01); *C12N 9/18* (2013.01); *C12Y 301/00* (2013.01); *C12Y 301/01074* (2013.01)

(58) Field of Classification Search
    USPC .................... 428/29; 283/94, 97, 114; 48/29
    See application file for complete search history.

(56) References Cited

U.S. PATENT DOCUMENTS

| | | | |
|---|---|---|---|
| 7,048,971 B2 | 5/2006 | Arora | 427/402 |
| 7,973,098 B2 * | 7/2011 | Reichelsheimer | B41M 3/14 |
| | | | 106/31.13 |
| 2009/0075085 A1 | 3/2009 | Reichelsheimer | 428/411.1 |

FOREIGN PATENT DOCUMENTS

| | | | | |
|---|---|---|---|---|
| KR | 10-2015-0077380 | 7/2015 | | |
| WO | WO 1999/008784 | 2/1999 | | |
| WO | WO 00/14601 A1 | 3/2000 | ............... | G03F 1/00 |
| WO | WO 2012/172172 | 12/2012 | | |
| WO | WO 2013/145772 | 10/2013 | | |

OTHER PUBLICATIONS

Japanese Office Action from corresponding Japanese Patent Application No. 2016-154408 dated Aug. 23, 2017.
Korean Office Action from corresponding Korean Patent Application No. 10-2015-0159856 dated Jun. 22, 2017.

\* cited by examiner

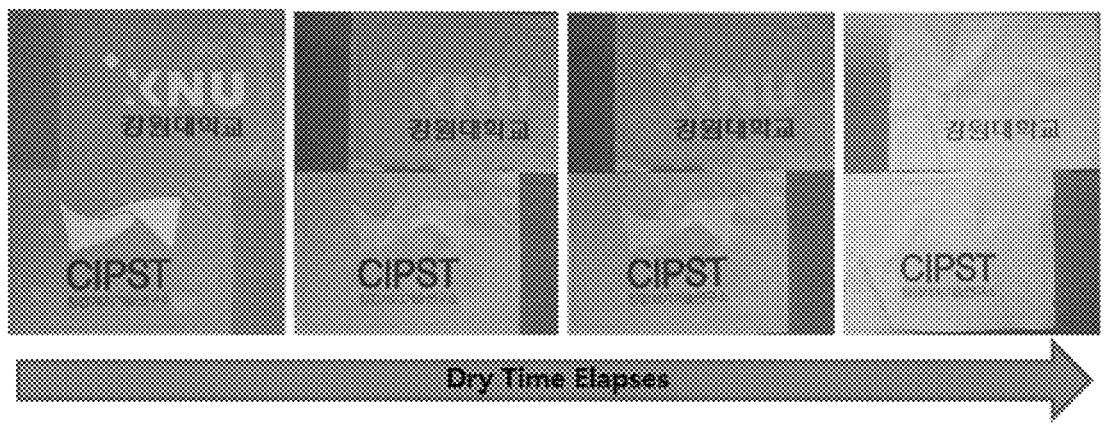

SYMPATHETIC PRINTED-MATTER AND METHOD OF PRODUCING THE SAME

CROSS REFERENCES TO RELATED APPLICATIONS

The present application claims the benefit and priority to Korean Patent Application No. 2015-0159856, filed in the Korean Patent Office on Nov. 13, 2015. The entire disclosure of the application is incorporated herein by reference.

FIELD

The present disclosure relates to a sympathetic printed-matter having a hydrophilic substrate portion formed on a hydrophobic substrate and a method of producing the same.

BACKGROUND

As industries are developing, and competitions become violent, demands for convenient and reliable steganography increase. In particular, a sympathetic printing method using a sympathetic ink promotes new demands for anti-forgery techniques in the field of securities or exchange checks. Sympathetic printed-matters using a sympathetic ink are advantageous in that a confidentiality status can be easily checked because whether or not a printed matter has been read by any other person can be easily confirmed. The term "sympathetic" means a phenomenon in which something is invisible on application or soon but can be visible later by developing the hidden parts. The sympathetic printed-matter is a printed matter produced using a sympathetic ink, on which a script written with a sympathetic ink can be visualized through heating or other methods such as a chemical reaction. The sympathetic ink may include a body fluid such as blood, saliva, sweat, and urine, various foods or compounds containing acidic or basic properties such as vinegar, fruit juice, sodium bicarbonate, salt, sugar, rice, aspirin, Arabian gum, boric acid, starch, ammonia, magnesium sulfate (epsom salts), caustic silver, soap, glue, or adhesive. As a representative material of the sympathetic ink, lead acetate ($Pb(CH_3COO)_2$) is known in the art. The lead acetate has a colorless crystalline material obtained by dissolving lead monoxide (PbO) or tri-lead tetra-oxide ($Pb_3O_4$) in acetic acid. A sympathetic ink is obtained by dissolving the lead acetate in an alum solution. As a method of visualizing hidden contents written on a sympathetic printed-matter, there are known an optical method in which a hidden part is visualized by irradiating light using a special light source such as infrared or ultraviolet rays or irradiating such light at a particular angle, a mechanical method in which a hidden part is visualized by dispersing minute powder such as graphite and sweeping away the powder, and a physical chemical method in which a hidden part is visualized by exposing the sympathetic printed-matter in the hot air, fumes, or vapors of a chemical agent or immersing it in a chemical agent. The sympathetic printed-matter using a sympathetic ink of the related art is based on an irreversible sympathetic phenomenon in which the printed part appears and does not disappear continuously thereafter. Even when it is reversible, it is difficult to know whether or not the hidden part of the sympathetic printed-matter has been already read by any other person. In addition, it is necessary to provide a separate reagent or tool for visualizing the hidden part on the sympathetic printed-matter.

CITATION LIST

Patent Literatures

[Patent Literature 1] Korean Patent No. 0173103

SUMMARY

In view of the aforementioned problems, the present disclosure provides a sympathetic printed-matter and a method of producing the same, by which a hidden part can be visualized just by wetting, and the visualized part disappears by removing water, so that it can be reused repeatedly. In addition, the present disclosure provides a sympathetic printed-matter having a reading confirmation portion by which whether or not the hidden part has been read by any other person can be easily confirmed.

According to an aspect of the present invention, there is provided a sympathetic printed-matter having a hydrophilic substrate portion formed on a hydrophobic substrate.

According to an embodiment of the invention, the sympathetic printed-matter is formed without using a sympathetic ink. In the sympathetic printed-matter according to the present invention, visualization is performed based on a brightness difference between a wetted substrate and an unwetted substrate. Therefore, the sympathetic ink is not necessary.

According to another embodiment of the invention, the hydrophobic substrate is obtained by performing fatty-acid-chloride gas grafting for a substrate formed of a material containing a hydroxyl group (—OH) to hydrophobize the substrate. Preferably, the substrate formed of a material containing the hydroxyl group (—OH) is cellulose or polyvinyl alcohol (PVA). More preferably, the substrate is a paper sheet or a paper board. Any substrate may be employed as long as it can be wetted by water. Considering print quality and use purposes, a paper sheet or a paper board having a high water absorption property is preferable. The fatty-acid-chloride grafting may be performed based on any gas grafting method known in the art (see, for example, Korean Patent Application Publication Nos. 10-2015-0077380 and 10-2015-0077379).

According to an implementation of the invention, the hydrophilic substrate portion is formed by partially printing an ester hydrolysis enzyme composition on the hydrophobic substrate. As a printing method of the enzyme composition, any method may be employed without a limitation as long as the enzyme composition can be printed on the hydrophobic substrate in a desired shape, and the enzyme composition can be sprayed uniformly with a constant thickness to uniformly generate the ester hydrolase reaction.

According to an implementation of the invention, the hydrophilic substrate portion additionally has a reading confirmation portion. The reading confirmation portion is used to irreversibly visualize whether or not a hidden part on the sympathetic printed-matter has been read by any other person.

According to another aspect of the invention, there is provided a method of printing a sympathetic printed-matter having a hydrophilic substrate portion formed on a hydrophobic substrate, the method including: (a) forming a hydrophobic substrate by performing gas grafting using fatty acid chloride; (b) partially printing an ester hydrolase composition of 0.3 to 0.7 $g/m^2$ on the hydrophobic substrate and generate a reaction for 20 to 40 minutes under a room temperature to form a hydrophilic substrate portion; (c) washing and drying the hydrophobic substrate having the hydrophilic substrate portion; and (d) printing a reading confirmation portion on the hydrophilic substrate portion.

Other objects and technical characteristics of the present invention will become apparent by reading the following description, claims, and drawings.

BRIEF DESCRIPTION OF THE DRAWINGS

The foregoing and additional features and characteristics of this disclosure will become more apparent from the following detailed description considered with reference to the accompanying drawings, wherein:

FIG. 1 illustrates a reversible sympathetic phenomenon of a sympathetic printed-matter.

DETAILED DESCRIPTION

The present disclosure provides a sympathetic printed-matter in which a hydrophobic substrate portion and a hydrophilic substrate portion are formed distinguishably, hidden contents are visualized by wetting, the hidden contents disappear by drying, and a reading confirmation portion is formed to allow a user to confirm whether or not the hidden contents have been read by any other person.

<Sympathetic Printed-Matter>

The term "sympathetic printed-matter" means a printed matter or sheet on which contents such as scripts, symbols, or pictures are invisible in ordinary times, and they are visualized when a particular condition is satisfied.

According to an embodiment of the invention, the sympathetic printed-matter exhibits a reversible sympathetic phenomenon depending on existence of water. The term "reversible" means that a sympathetic property can be repeatedly exhibited under a particular condition. In the sympathetic printed-matter according to the present invention, hidden contents are visualized under a particular condition such as a moisture increase (wetted or immersed condition), and they disappear when the moisture is removed. A sympathetic printed-matter of the related art is printed using a sympathetic ink. Since the sympathetic ink is formed of metal salts, acids, or bases, special reagent or equipment is necessary to produce the sympathetic ink. However, the sympathetic printed-matter according to the present invention is produced without using the sympathetic ink. Therefore, it is possible to reduce cost for the sympathetic ink. In addition, the sympathetic ink used in the sympathetic printed-matter of the related art has an irreversible sympathetic property. Therefore, the sympathetic printed-matter of the related art is discarded after the hidden contents are visualized. However, the sympathetic printed-matter according to the present invention exhibits a reversible sympathetic property depending on existence of water. Therefore, it can be reused repeatedly.

<Substrates of Sympathetic Printed-Matter>

The sympathetic phenomenon according to the present invention is caused by characteristics of substrates. A wet substrate and a dry substrate have different light scattering properties. A dry substrate has a high light scattering rate, and this makes bright appearance. A wet substrate has a low light scattering rate, and this makes dark appearance. Based on this principle, a dry substrate and a wet substrate can be easily distinguished. The sympathetic phenomenon of the sympathetic printed-matter according to the present invention is based on the aforementioned principle.

According to an embodiment of the invention, a hydrophobic substrate is obtained by performing fatty-acid-chloride gas grafting for a substrate formed of a material containing a hydroxyl group (—OH) to hydrophobize the substrate. The substrate formed of a material containing a hydroxyl group (—OH) may include cellulose or polyvinyl alcohol (PVA). Preferably, the substrate is a paper sheet or a paper board. Since the substrate formed of a material containing a hydroxyl group (—OH) is hydrophilic, it can absorb water and can be hydrophobized through the fatty-acid-chloride gas grafting.

According to an implementation of the invention, the sympathetic printed-matter includes an unwettable hydrophobic substrate formed through fatty-acid-chloride gas grafting and a wettable hydrophilic substrate portion formed on the hydrophobic substrate. Therefore, if the sympathetic printed-matter is wetted or immersed in water, the wetted hydrophilic substrate portion appears dark, and the unwetted hydrophobic substrate appears bright. Therefore, if contents such as scripts, pictures, or symbols are written on the hydrophobic substrate, the contents on the hydrophobic substrate are visualized brightly when the hydrophilic substrate portion absorbs water. In addition, a brightness difference of the hydrophilic substrate portion due to water absorption is removed when the water is dried away. Therefore, the sympathetic phenomenon of the sympathetic printed-matter is reversible. As described above, in order to visualize contents such as scripts, pictures, or symbols on the basis of a water absorption property, the substrate is required to basically have an excellent water absorption property and be susceptible to hydrophobization through fatty-acid-chloride gas grafting.

<Hydrophobic Substrate of Sympathetic Printed-Matter>

According to an implementation of the invention, the hydrophobic substrate is hydrophobized through fatty-acid-chloride gas grafting.

According to the present invention, the term "fatty-acid-chloride gas grafting" means a reaction between a fatty-acid-chloride gas and a hydroxyl group (—OH) of the hydrophilic substrate to form fatty acid ester on the substrate and produce hydrogen chloride as by-product as expressed in the following Expression 1. This reaction is discussed in detail in U.S. Pat. No. 6,342,268.

$$S-OH + RCOCl \Leftrightarrow S-O-CO-R + HCl \qquad [\text{Expression 1}]$$

If the fatty acid ester is formed through fatty-acid-chloride gas grafting on the substrate, the substrate is hydrophobized.

According to an implementation of the invention, the fatty acid chloride may include a mixture containing at least an element selected from a group consisting of, but not limited to, myristoleic acid, palmitoleic acid, palmitoyl chloride, sapienic acid, oleic acid, eladic acid, vaccenic acid, linoleic acid, linoelaidic acid, α-linolenic acid, arachidonic acid, eicosapentanoic acid, erucic acid, docosahexaenoic acid, caprylic acid, capric acid, lauric acid, myristic acid, palmitic acid, stearic acid, stearoyl chloride, arachidic acid, behenic acid, lignoceric acid, or cerotic acid. Preferably, the fatty acid chloride is a mixture of palmitoyl chloride (C16) and stearoyl chloride (C18). If a molecular weight of the fatty acid chloride is small, vaporization is easily generated, so that the gas grafting can be facilitated. However, hydrophobization may be short due to ester bonds of the fat acid ester. In contrast, a molecular weight of the fatty acid chloride is large, hydrophobization is excellent, but vaporization is not easily generated, so that gas grafting is delayed. In order to overcome such shortcomings, a mixture of fatty acid chloride having a small molecular weight and fatty acid chloride having a large molecular weight, for example, a mixture of palmitoyl chloride (C16) and stearoyl chloride (C18) is employed. As a result, it is possible to perform a multi-stage hydrophobizing reaction capable of improving hydrophobization efficiency while obtaining both advantages of two types of fatty acid chlorides. The multi-stage hydrophobizing reaction described above is advantageous in that palmitoyl chloride (C16) that can be easily vaporized is primarily reacted with the hydroxyl group for hydrophobization when a temperature of the paper sheet coated with fatty acid chloride is not sufficiently raised in an initial stage of the reaction, and stearoyl chloride (C18) participates in the hydrophobization reaction when the temperature of the paper sheet sufficiently increases.

According to an embodiment of the invention, the fatty-acid-chloride gas grafting may be performed using a fatty-acid-chloride gas grafting facility provided with an anilox roller. The fatty-acid-chloride gas grafting facility provided with an anilox roller is based on a gravure print technique and is suitable for large-amount print works. The fatty-acid-chloride gas grafting facility may be driven for a filter paper having a basis weight of 50 to 90 g by setting an anilox roller temperature to 40 to 80° C., setting a coat amount to 0.3 to 0.7 g/m$^2$, setting a dry roller temperature to 170 to 210° C., setting a hot air temperature for air knife flushing to 280 to 320° C., and setting a driving speed to 30 to 70 m/min. Preferably, the fatty-acid-chloride gas grafting facility is driven for a filter paper having a basis weight of 70 g by setting an anilox roller temperature to 60° C., setting a coat amount to 0.5 g/m$^2$, setting a dry roller temperature to 190° C., setting a hot air temperature for air knife flushing to 300° C., and setting a driving speed to 50 m/min.

<Hydrophilic Substrate Portion of Sympathetic Printed-Matter>

According to an implementation of the invention, the hydrophilic substrate portion of the sympathetic printed-matter is formed by partially printing an ester hydrolase composition on the hydrophobic substrate described above.

According to an implementation of the invention, the ester hydrolase composition is a composition containing at least an enzyme selected from a group consisting of esterase, lipase, cutinase, azolesterase, tannase, chlorophyllase, phospholipase, phosphatase, or sulfatase.

In the ester hydrolase composition described above, the ester bonds of fatty acid ester existing on a surface of the hydrophobic substrate are broken by fatty acid chlorides, so that hydrophobic property of the substrate is reduced, and the hydrophilic property is improved. For example, the lipase acts to remove ester bonds of the fatty acid ester as expressed in the following Expression 2.

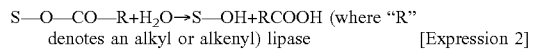

S—O—CO—R+H$_2$O→S—OH+RCOOH (where "R" denotes an alkyl or alkenyl) lipase    [Expression 2]

Modification efficiency (modification rate) in the conversion from the hydrophobic substrate to the hydrophilic substrate portion may be determined depending on enzymatic activity of the enzyme composition, the amount of a ground substance, contact frequency between the enzyme composition and the ground substance (fatty acid chlorides), and a reaction temperature. In order to obtain high modification rate from the hydrophobic substrate to the hydrophilic substrate portion, it is required to spray a sufficient amount of the enzyme composition through printing to provide enzymatic activity suitable for the fatty acid ester existing in the hydrophobic substrate. In addition, it is required that the sprayed enzyme composition be sufficiently absorbed in the substrate to break ester bonds of fatty acid ester formed in the substrate. Therefore, the spray amount of the enzyme composition may be determined depending on the amount of fatty acid chlorides coated through the fatty-acid-chloride gas grafting.

According to an embodiment of the invention, the spray amount of the enzyme composition is preferably set to one or more times that of the coated fatty acid chlorides, which is enough to wet the surface. The breaking of ester bonds caused by the enzyme composition depends on time and temperature. Therefore, as the reaction time increases, and the temperature increases up to 55° C., the reaction is more promoted as long as the liquid enzyme is not dried. If the liquid enzyme composition is initially sprayed on the surface hydrophobized through fatty-acid-chloride gas grafting, penetration of the enzyme composition becomes difficult, and breaking of ester bonds is limited on the sprayed surface. However, as the reaction time increases, and the hydrophilic property of the hydrophobic substrate gradually increases, the enzyme composition more penetrates into the substrate, so that the breaking of ester bonds is generated in a wider area. Therefore, if the enzyme composition is excessively sprayed, the hydrophilization reaction caused by the enzyme composition is generated in a wider area, so that a resolution of the sympathetic printed-matter may be degraded. In addition, under an excessively high temperature where the enzyme composition is dried fast, activity may be reduced before the enzyme breaks ester bonds.

According to an embodiment of the invention, the enzyme composition is sprayed on the hydrophobic substrate at a concentration of 0.3 to 0.7 g/m$^2$. Preferably, the enzyme composition is sprayed on the hydrophobic substrate at a concentration of 0.5 g/m$^2$.

According to another embodiment of the invention, the enzyme composition is reacted for 20 to 40 minutes under a room temperature. Preferably, the enzyme composition is reacted for 30 minutes under a room temperature.

As a method of printing the ester hydrolase composition on the hydrophobic substrate, various printing methods used in printing of scripts, pictures, and patterns on a paper sheet may be employed. The printing method according to the present invention may include, for example, a relief printing method such as ink-jet print, letterpress print, line engraving print, photogravure print, and duplication print, a planographic printing method such as a direct drawing print, transfer print, albumen print, deep etch print, multi-layer plate print, and presensitized (PS) print, and an intaglio printing method such as a copper-plate engraving print or gravure engraving print, but not limited thereto. Preferably, the printing method according to the present invention is an ink-jet printing method.

<Reading Confirmation Portion of Sympathetic Printed-Matter>

According to an implementation of the invention, the hydrophilic substrate portion additionally has a reading confirmation portion. The reading confirmation portion is printed on the hydrophilic substrate portion to indicate whether or not hidden contents on the sympathetic printed-matter have been read by any other person. Any display type may be employed without a limitation as long as a shape or a physical property is changed by water to indicate the reading confirmation. The reading confirmation portion may be printed using a hydrophilic pigment. In the reading confirmation portion formed using a hydrophilic pigment, the hydrophilic pigment spreads by water to provide a different color or shape and indicate the reading confirmation. The reading confirmation portion may exhibit the sympathetic phenomenon. However, the sympathetic phenomenon of the reading confirmation portion is preferably irreversible.

<Sympathetic Printing Method>

A method of printing a sympathetic printed-matter having a hydrophilic substrate portion formed on a hydrophobic substrate according to another aspect of the present invention will be described.

First, a substrate susceptible to the fatty-acid-chloride gas grafting is selected and is cut to a suitable size. The substrate may be a hydrophilic substrate formed of a material containing a hydroxyl group (—OH). Preferably, the substrate may include a paper sheet containing cellulose or polyvinyl alcohol. Alternatively, any hydrophilic substrate may be employed without a limitation as long as it is formed of a material containing a hydroxyl group and has an excellent water absorption property.

According to an embodiment of the invention, the substrate may be a filter paper having a basis weight of 60 to 80 g. Preferably, the substrate is a filter paper having a basis weight of 70 g.

According to an implementation of the invention, fatty-acid-chloride gas grafting is performed on a surface of the substrate prepared as described above to form a hydrophobic substrate. The formation of the hydrophobic substrate has been described above in the chapter "Hydrophobic Substrate Portion of Sympathetic Printed-Matter," and will not be described for simplicity purposes.

According to an embodiment of the invention, an ester hydrolase composition is partially printed on the hydrophobic substrate to form a hydrophilic substrate portion.

The print amount of the enzyme composition is preferably set to one or more times that of the coated fatty acid chloride, which is enough to wet the surface.

The enzyme composition may be printed and sprayed on the hydrophobic substrate using an ink-jet printer. The amount of the sprayed enzyme composition may be determined depending on enzymatic activity of the enzyme composition, the amount of a ground substance, contact frequency between the enzyme composition and the ground substance (fatty acid chlorides), and a reaction temperature. The amount of the sprayed enzyme composition is preferably set such that the enzyme composition is sufficiently absorbed in the substrate to break all of the ester bonds of fatty acid ester formed in the substrate.

According to an embodiment of the invention, the ester hydrolase composition is printed on the hydrophobic substrate at a concentration of 0.3 to 0.7 $g/m^2$ and is reacted for 20 to 40 minutes under a room temperature to form a hydrophilic substrate portion. Preferably, an ester hydrolase composition is printed on the hydrophobic substrate at a concentration of 0.5 $g/m^2$ and is reacted for 30 minutes under a room temperature to form a hydrophilic substrate portion.

According to another implementation of the invention, the ester hydrolase composition is a composition containing at least an enzyme selected from a group consisting of esterase, lipase, cutinase, azolesterase, tannase, chlorophyllase, phospholipase, phosphatase, or sulfatase.

According to another embodiment of the invention, a hydrophilic modification rate of the hydrophilic substrate portion formed using the enzyme composition may be evaluated indirectly using a Cobb sizing test.

According to another implementation of the invention, the hydrophobic substrate having the hydrophilic substrate portion is washed and dried. Through the washing and drying process, the reaction of the sprayed enzyme composition stops. Therefore, it is possible to prevent degradation of the resolution of the hidden contents. The washing may be performed until the enzyme composition existing on the hydrophilic substrate is removed to eliminate activity. The drying may be performed until the reading confirmation portion can be printed.

According to an implementation of the invention, the reading confirmation portion is printed on the hydrophilic substrate portion. The reading confirmation portion may be printed in a similar way to that of the method of printing the enzyme composition. The reading confirmation portion may exhibit a sympathetic phenomenon. The sympathetic phenomenon of the reading confirmation portion is preferably irreversible. For example, the reading confirmation portion may be printed with a hydrophilic ink, so that the reading confirmation can be visualized by wetting the sympathetic printed-matter and colorizing the hidden contents through spreading.

EXAMPLES

1. Example 1: Sympathetic Printed-Matter Using Lipase

Hydrophobization treatment was performed by utilizing a fatty-acid-chloride gas grafting facility established in a release-paper manufacturing factory (T-company) located in Dong-doo-cheon, Kyung-ki-do, South Korea. Fatty acid chloride was coated on a filter paper having a basis weight of 70 g, and the coat amount of the anilox roller was adjusted to 0.5 $g/m^2$. The fatty acid chloride was a mixture of palmitoyl chloride (C16) and stearoyl chloride (C18). A temperature of the anilox (gravure) roller was fixed to 60° C., and a temperature of a dry roller was adjusted to 190° C. A temperature of the hot air for air knife flushing was set to 300° C. Under the treatment condition described above, hydrophobization treatment was performed by fixing a driving speed of the facility to 50 m/min. Then, enzyme printing was performed for the filter paper subjected to the treatment. As the enzyme, preferably, esterase having ester bonds is employed. More preferably, any one of lipase and cutinase or a mixture thereof is employed from the viewpoint of improvement of a yield against a treatment cost. In Example 1, a product name, Resinase A2X (produced by Novozymes. Denmark) was used as lipase originated from *thermomyces lanuginosus*. An undiluted solution of enzyme (enzyme composition) was sprayed on the filter paper hydrophobized through the fatty-acid-chloride gas grafting at a concentration of 0.5 $g/m^2$ and was reacted for 30 minutes under a room temperature. In order to compare an absorption rate of the hydrophobized filter paper and an absorption rate of the filter paper subjected to the hydrophobization and the enzyme treatment, a Cobb sizing test was performed after 30 minutes. The measurement result is shown in the following Table 1. The following Table 1 shows the measurement result of the Cobb sizing test for an original filter paper, a filter paper subjected to fatty acid chloride hydrophobization treatment, and a hydrophobized filter paper subjected to enzyme hydrolysis treatment.

2. Example 2: Sympathetic Printed-Matter Using Cutinase

Hydrophobization treatment was performed by utilizing a fatty-acid-chloride gas grafting facility established in a release-paper manufacturing factory (T-company) located in Dong-doo-cheon, Kyung-ki-do, South Korea. Fatty acid chloride was coated on a filter paper having a basis weight of 70 g, and the coat amount of the anilox roller was adjusted to 0.5 g/m². The fatty acid chloride was a mixture of palmitoyl chloride (C16) and stearoyl chloride (C18). A temperature of the anilox (gravure) roller was fixed to 60° C., and a temperature of a dry roller was adjusted to 190° C. A temperature of the hot air for air knife flushing was set to 300° C. Under the treatment condition described above, hydrophobization treatment was performed by fixing a driving speed of the facility to 50 m/min. Then, enzyme printing was performed for the filter paper subjected to the treatment. In Example 2, a product name, Optimyze (produced by Buckman Laboratories, USA) was used as cutin-hydrolase representing a hydrolase for a cuticle layer originated from *magnaporthe grisea*. An undiluted solution of enzyme was sprayed on the filter paper hydrophobized through the fatty-acid-chloride gas grafting at a concentration of 0.5 g/m². An undiluted solution of enzyme was sprayed on the filter paper hydrophobized through the fatty-acid-chloride gas grafting at a concentration of 0.5 g/m², and the filter paper was laid aside for 30 minutes under a room temperature. In order to compare an absorption rate of the hydrophobized filter paper and an absorption rate of the filter paper subjected to the hydrophobization and the enzyme treatment, a Cobb sizing test was performed after 30 minutes. The measurement result is shown in the following Table 1. The following Table 1 shows the measurement result of the Cobb sizing test for an original filter paper, a filter paper subjected to the fatty-acid-chloride hydrophobization treatment, and a hydrophobized filter paper subjected to the enzyme hydrolysis treatment.

3. Comparison of Examples

Referring to Table 1, it is recognized that the Cobb size value abruptly increases in both Examples 1 and 2 after the hydrophobization treatment. This result means that the filter paper is hydrophobized through the fatty-acid-chloride gas grafting reaction so as not to absorb water. In the example, the fatty-acid-chloride gas grafting is performed for the filter paper, and then, the hydrolysis treatment using lipase and cutinase was performed for that filter paper. Comparing the Cobb sizing values for the filter papers, it is recognized that the hydrophilic property of the filter paper of Example 1 is better than that of Example 2. It is conceived that this is because activities of lipase and cutinase measured from the decomposition rate of the p-nitro phenyl myristate were 35,056 units/mL and 14,974 units/mL, respectively, which shows that the activity of Example 1 using lipase is double or more times than that of Example 2 using cutinase.

4. Reversible Sympathetic Printed-Matter

As described above, the filter paper hydrophobized through the fatty-acid-chloride gas grafting reaction was hydrophilized using esterase to obtain a sympathetic printed-matter. As shown in FIG. 1, it was recognized that hidden contents such as scripts or pictures can be visualized in a wetted or unwetted portion by immersing the paper sheet subjected to the treatment in water. In addition, it was recognized that the pictures or scripts disappear by drying the water. Therefore, it was possible to obtain a reversible sympathetic printed-matter. If a part of the sympathetic printed-matter described above is printed or colorized using a hydrophilic pigment to form a reading confirmation portion, it is possible to easily confirm whether or not the hidden contents on the sympathetic printed-matter have been read by any other person.

Using the sympathetic printed-matter according to the present invention, a hidden part can be visualized just by wetting. Therefore, it is possible to remove necessities of the sympathetic ink and a material such as reagent or equipment for visualizing the hidden part. In addition, since the visualized hidden content disappears by removing water from the sympathetic printed-matter, the sympathetic printed-matter can be reused repeatedly. Using the reading confirmation portion, whether or not the sympathetic printed-matter has been read by any other person can be easily confirmed. In the sympathetic printing method according to the present invention, a hydrophobic substrate can be formed using an existing gas grafting facility, and an ester hydrolase composition and the reading confirmation portion can be formed using an existing printing method. Therefore, a large amount of sympathetic printed-matters can be produced inexpensively and efficiently.

Although exemplary embodiments of the present invention have been shown and described hereinbefore, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

What is claimed is:

1. A sympathetic printed-matter having a hydrophilic substrate portion formed on a hydrophobic substrate,
    wherein the hydrophobic substrate is subjected to fatty-acid-chloride gas grafting to perform hydrophobization treatment, and
    wherein the hydrophilic substrate portion is formed by partially printing an ester hydrolase composition on the hydrophobic substrate.

2. The sympathetic printed-matter according to claim 1, wherein the hydrophobic substrate is subjected to fatty-acid-chloride gas grafting to perform hydrophobization treatment.

3. The sympathetic printed-matter according to claim 2, wherein the fatty acid chloride is a mixture containing at least an element selected from a group consisting of myristoleic acid, palmitoleic acid, palmitoyl chloride, sapienic acid, oleic acid, eladic acid, vaccenic acid, linoleic acid, linoelaidic acid, α-linolenic acid, arachidonic acid, eicosapentanoic acid, erucic acid, docosahexaenoic acid, caprylic acid, capric acid, lauric acid, myristic acid, palmitic acid, stearic acid, stearoyl chloride, arachidic acid, behenic acid), lignoceric acid, or cerotic acid.

4. The sympathetic printed-matter according to claim 1, wherein the hydrophilic substrate portion is formed by partially printing an ester hydrolase composition on the hydrophobic substrate.

5. The sympathetic printed-matter according to claim 4, wherein the ester hydrolase composition is a mixture containing at least an enzyme selected from a group consisting of esterase, lipase, cutinase, azolesterase, tannase, chlorophyllase, phospholipase, phosphatase, or sulfatase.

6. The sympathetic printed-matter according to claim 1, wherein the hydrophilic substrate further includes a reading confirmation portion.

7. The sympathetic printed-matter according to claim 1, wherein the fatty acid chloride is a mixture containing at least an element selected from a group consisting of myristoleic acid, palmitoleic acid, palmitoyl chloride, sapienic acid, oleic acid, eladic acid, vaccenic acid, linoleic acid, linoelaidic acid, α-linolenic acid, arachidonic acid, eicosapentanoic acid, erucic acid, docosahexaenoic acid, caprylic acid, capric acid, lauric acid, myristic acid, palmitic acid, stearic acid, stearoyl chloride, arachidic acid, behenic acid), lignoceric acid, or cerotic acid.

8. The sympathetic printed-matter according to claim 1, wherein the ester hydrolase composition is a mixture containing at least an enzyme selected from a group consisting of esterase, lipase, cutinase, azolesterase, tannase, chlorophyllase, phospholipase, phosphatase, or sulfatase.

9. The sympathetic printed-matter according to claim 1, wherein the hydrophilic substrate further includes a reading confirmation portion.

10. A method of printing a sympathetic printed-matter having a hydrophilic substrate portion formed on a hydrophobic substrate, the method comprising:
(a) forming a hydrophobic substrate by performing gas grafting using fatty acid chloride;
(b) partially printing an ester hydrolase composition on the hydrophobic substrate to form a hydrophilic substrate portion;
(c) washing and drying the hydrophobic substrate having the hydrophilic substrate portion; and
(d) printing a reading confirmation portion on the hydrophilic substrate portion.

11. The method according to claim 10, wherein the fatty acid chloride is a mixture containing at least an element selected from a group consisting of myristoleic acid, palmitoleic acid, palmitoyl chloride, sapienic acid, oleic acid, eladic acid, vaccenic acid, linoleic acid, linoelaidic acid, α-linolenic acid, arachidonic acid, eicosapentanoic acid, erucic acid, docosahexaenoic acid, caprylic acid, capric acid, lauric acid, myristic acid, palmitic acid, stearic acid, stearoyl chloride, arachidic acid, behenic acid), lignoceric acid, or cerotic acid.

12. The method according to claim 10, wherein the ester hydrolase composition is a mixture containing at least an enzyme selected from a group consisting of esterase, lipase, cutinase, azolesterase, tannase, chlorophyllase, phospholipase, phosphatase, or sulfatase.

* * * * *